United States Patent
Wiegand et al.

(10) Patent No.: US 7,309,483 B2
(45) Date of Patent: Dec. 18, 2007

(54) METHOD OF TREATMENT USING TIE2 LIGAND2

(75) Inventors: Stanley J. Wiegand, Croton-on-Hudson, NY (US); Peter A. Campochiaro, Baltimore, MD (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 247 days.

(21) Appl. No.: 11/073,091

(22) Filed: Mar. 4, 2005

(65) Prior Publication Data

US 2005/0175617 A1    Aug. 11, 2005

Related U.S. Application Data

(63) Continuation of application No. 10/186,817, filed on Jul. 1, 2002, now abandoned, which is a continuation-in-part of application No. 09/442,717, filed on Nov. 18, 1999, now Pat. No. 6,627,415, which is a continuation of application No. 08/930,721, filed as application No. PCT/US96/04806 on Apr. 5, 1996, now abandoned.

(51) Int. Cl.
*A61K 38/19* (2006.01)

(52) U.S. Cl. .............................. 424/85.1; 514/2; 514/8; 514/12

(58) Field of Classification Search ..................... None
See application file for complete search history.

(56) References Cited

OTHER PUBLICATIONS

Suri, et al., "Requisite Role of Angiopoietin-1, a Ligand for the TIE2 Receptor, During Embryonic Angiogenesis", Cell 87:1171-1180, 1996.
Maisonpierre, et al., "Angiopoietin-2, a Natural Antagonist for Tie2 that Disrupts In Vivo Angiogenesis", Science 277:55-60, 1997.
Hackett, et al., "Angiopoietin 2 Expression in the Retina: Upregulation During Physiologic and Pathologic Neovascularization", Journal of Cellular Physiology 184:275-284, 2000.

*Primary Examiner*—Prema Mertz
(74) *Attorney, Agent, or Firm*—Valeta Gregg, Esq.

(57) ABSTRACT

The invention provides for therapeutic compositions as well as a method of blocking blood vessel growth, a method of promoting neovascularization, a method of promoting the growth or differentiation of a cell expressing the TIE-2 receptor, a method of blocking the growth or differentiation of a cell expressing the TIE-2 receptor and a method of attenuating or preventing tumor growth in a human.

3 Claims, 3 Drawing Sheets

Fig. 2A

```
          10        20        30        40        50        60        70        80
           •         •         •         •         •         •         •         •
GAATTCCTGGGTTGGTGTTTATCTCCTCCCAGCCTTGAGGGAGGGAACAACACTGTAGGATCTGGGAGAGAGGAACAAA 90       100       110       120       130       140       150       160
           •         •         •         •         •         •         •         •
GGACCGTGAAAGCTGCTCTGTAAAAGCTGACACAGCCCTCCCAAGTGAGCAGGACTGTTCTTCCCACTGCAATCTGACAG 170       180       190       200       210       220       230       240
           •         •         •         •         •         •         •         •
TTTACTGCATGCCTGGAGAGAACACAGCAGTAAAAACCAGGTTTGCTACTGGAAAAAGAGGAAAGAGAAGACTTTCATTG 250       260       270       280       290       300       310       320
           •         •         •         •         •         •         •         •
ACGGACCCAGCCATGGCAGCGTAGCAGCCCTGCGTTTCAGACGGCAGCAGCTCGGGACTCTGGACGTGTGTTTGCCCTCA 330       340       350       360       370       380
           •         •         •         •         •         •
AGTTTGCTAAGCTGCTGGTTTATTACTGAAGAAAGA ATG TGG CAG ATT GTT TTC TTT ACT CTG AGC TGT
                                      M   W   Q   I   V   F   F   T   L   S   C>

390       400       410       420       430       440
 •         •         •         •         •         •
GAT CTT GTC TTG GCC GCA GCC TAT AAC AAC TTT CGG AAG AGC ATG GAC AGC ATA GGA AAG
 D   L   V   L   A   A   A   Y   N   N   F   R   K   S   M   D   S   I   G   K>

450       460       470       480       490       500
 •         •         •         •         •         •
AAG CAA TAT CAG GTC CAG CAT GGG TCC TGC AGC TAC ACT TTC CTC CTG CCA GAG ATG GAC
 K   Q   Y   Q   V   Q   H   G   S   C   S   Y   T   F   L   L   P   E   M   D>

510       520       530       540       550       560
 •         •         •         •         •         •
AAC TGC CGC TCT TCC TCC AGC CCC TAC GTG TCC AAT GCT GTG CAG AGG GAC GCG CCG CTC
 N   C   R   S   S   S   S   P   Y   V   S   N   A   V   Q   R   D   A   P   L>

570       580       590       600       610       620
 •         •         •         •         •         •
GAA TAC GAT GAC TCG GTG CAG AGG CTG CAA GTG CTG GAG AAC ATC ATG GAA AAC AAC ACT
 E   Y   D   D   S   V   Q   R   L   Q   V   L   E   N   I   M   E   N   N   T>

630       640       650       660       670       680
 •         •         •         •         •         •
CAG TGG CTA ATG AAG CTT GAG AAT TAT ATC CAG GAC AAC ATG AAG AAA GAA ATG GTA GAG
 Q   W   L   M   K   L   E   N   Y   I   Q   D   N   M   K   K   E   M   V   E>

690       700       710       720       730       740
 •         •         •         •         •         •
ATA CAG CAG AAT GCA GTA CAG AAC CAG ACG GCT GTG ATG ATA GAA ATA GGG ACA AAC CTG
 I   Q   Q   N   A   V   Q   N   Q   T   A   V   M   I   E   I   G   T   N   L>

750       760       770       780       790       800
 •         •         •         •         •         •
TTG AAC CAA ACA GCT GAG CAA ACG CGG AAG TTA ACT GAT GTG GAA GCC CAA GTA TTA AAT
 L   N   Q   T   A   E   Q   T   R   K   L   T   D   V   E   A   Q   V   L   N>

810       820       830       840       850       860
 •         •         •         •         •         •
CAG ACC ACG AGA CTT GAA CTT CAG CTC TTG GAA CAC TCC CTC TCG ACA AAC AAA TTG GAA
 Q   T   T   R   L   E   L   Q   L   L   E   H   S   L   S   T   N   K   L   E>

870       880       890       900       910       920
 •         •         •         •         •         •
AAA CAG ATT TTG GAC CAG ACC AGT GAA ATA AAC AAA TTG CAA GAT AAG AAC AGT TTC CTA
 K   Q   I   L   D   Q   T   S   E   I   N   K   L   Q   D   K   N   S   F   L>

930       940       950       960       970       980
 •         •         •         •         •         •
GAA AAG AAG GTG CTA GCT ATG GAA GAC AAG CAC ATC ATC CAA CTA CAG TCA ATA AAA GAA
 E   K   K   V   L   A   M   E   D   K   H   I   I   Q   L   Q   S   I   K   E>

990      1000      1010      1020      1030      1040
 •         •         •         •         •         •
GAG AAA GAT CAG CTA CAG GTG TTA GTA TCC AAG CAA AAT TCC ATC ATT GAA GAA CTA GAA
 E   K   D   Q   L   Q   V   L   V   S   K   Q   N   S   I   I   E   E   L   E>

1050      1060      1070      1080      1090      1100
 •         •         •         •         •         •
AAA AAA ATA GTG ACT GCC ACG GTG AAT AAT TCA GTT CTT CAA AAG CAG CAA CAT GAT CTC
 K   K   I   V   T   A   T   V   N   N   S   V   L   Q   K   Q   Q   H   D   L>
```

Fig. 2B

```
       1110        1120        1130        1140        1150        1160
         •           •           •           •           •           •
      ATG GAG ACA GTT AAT AAC TTA CTG ACT ATG ATG TCC ACA TCA AAC TCA GCT AAG GAC CCC
       M   E   T   V   N   N   L   L   T   M   M   S   T   S   N   S   A   K   D   P>

1170        1180        1190        1200        1210        1220
         •           •           •           •           •           •
      ACT GTT GCT AAA GAA GAA CAA ATC AGC TTC AGA GAC TGT GCT GAA GTA TTC AAA TCA GGA
       T   V   A   K   E   E   Q   I   S   F   R   D   C   A   E   V   F   K   S   G>

1230        1240        1250        1260        1270        1280
         •           •           •           •           •           •
      CAC ACC ACA AAT GGC ATC TAC ACG TTA ACA TTC CCT AAT TCT ACA GAA GAG ATC AAG GCC
       H   T   T   N   G   I   Y   T   L   T   F   P   N   S   T   E   E   I   K   A>

1290        1300        1310        1320        1330        1340
         •           •           •           •           •           •
      TAC TGT GAC ATG GAA GCT GGA GGA GGC GGG TGG ACA ATT ATT CAG CGA CGT GAG GAT GGC
       Y   C   D   M   E   A   G   G   G   G   W   T   I   I   Q   R   R   E   D   G>

1350        1360        1370        1380        1390        1400
         •           •           •           •           •           •
      AGC GTT GAT TTT CAG AGG ACT TGG AAA GAA TAT AAA GTG GGA TTT GGT AAC CCT TCA GGA
       S   V   D   F   Q   R   T   W   K   E   Y   K   V   G   F   G   N   P   S   G>

1410        1420        1430        1440        1450        1460
         •           •           •           •           •           •
      GAA TAT TGG CTG GGA AAT GAG TTT GTT TCG CAA CTG ACT AAT CAG CAA CGC TAT GTG CTT
       E   Y   W   L   G   N   E   F   V   S   Q   L   T   N   Q   Q   R   Y   V   L>

1470        1480        1490        1500        1510        1520
         •           •           •           •           •           •
      AAA ATA CAC CTT AAA GAC TGG GAA GGG AAT GAG GCT TAC TCA TTG TAT GAA CAT TTC TAT
       K   I   H   L   K   D   W   E   G   N   E   A   Y   S   L   Y   E   H   F   Y>

1530        1540        1550        1560        1570        1580
         •           •           •           •           •           •
      CTC TCA AGT GAA GAA CTC AAT TAT AGG ATT CAC CTT AAA GGA CTT ACA GGG ACA GCC GGC
       L   S   S   E   E   L   N   Y   R   I   H   L   K   G   L   T   G   T   A   G>

1590        1600        1610        1620        1630        1640
         •           •           •           •           •           •
      AAA ATA AGC AGC ATC AGC CAA CCA GGA AAT GAT TTT AGC ACA AAG GAT GGA GAC AAC GAC
       K   I   S   S   I   S   Q   P   G   N   D   F   S   T   K   D   G   D   N   D>

1650        1660        1670        1680        1690        1700
         •           •           •           •           •           •
      AAA TGT ATT TGC AAA TGT TCA CAA ATG CTA ACA GGA GGC TGG TGG TTT GAT GCA TGT GGT
       K   C   I   C   K   C   S   Q   M   L   T   G   G   W   W   F   D   A   C   G>

1710        1720        1730        1740        1750        1760
         •           •           •           •           •           •
      CCT TCC AAC TTG AAC GGA ATG TAC TAT CCA CAG AGG CAG AAC ACA AAT AAG TTC AAC GGC
       P   S   N   L   N   G   M   Y   Y   P   Q   R   Q   N   T   N   K   F   N   G>

1770        1780        1790        1800        1810        1820
         •           •           •           •           •           •
      ATT AAA TGG TAC TAC TGG AAA GGC TCA GGC TAT TCG CTC AAG GCC ACA ACC ATG ATG ATC
       I   K   W   Y   Y   W   K   G   S   G   Y   S   L   K   A   T   T   M   M   I>

1830        1840        1850        1860        1870        1880        1890        1900
         •           •           •           •           •           •           •           •
      CGA CCA GCA GAT TTC TAAACATCCCAGTCCACCTGAGGAACTGTCTCGAACTATTTTCAAAGACTTAAGCCCAGT
       R   P   A   D   F>

1910        1920        1930        1940        1950        1960        1970        1980
               •           •           •           •           •           •           •           •
      GCACTGAAAGTCACGGCTGCGCACTGTGTCCTCTTCCACCACAGAGGGCGTGTGCTCGGTGCTGACGGGACCCACATGCT 1990        2000        2010        2020        2030        2040        2050        2060
               •           •           •           •           •           •           •           •
      CCAGATTAGAGCCTGTAAACTTTATCACTTAAACTTGCATCACTTAACGGACCAAAGCAAGACCCTAAACATCCATAATT 2070        2080        2090        2100        2110        2120        2130        2140
               •           •           •           •           •           •           •           •
      GTGATTAGACAGAACACCTATGCAAAGATGAACCCGAGGCTGAGAATCAGACTGACAGTTTACAGACGCTGCTGTCACAA 2150        2160        2170        2180        2190        2200        2210        2220
               •           •           •           •           •           •           •           •
      CCAAGAATGTTATGTGCAAGTTTATCAGTAAATAACTGGAAAACAGAACACTTATGTTATACAATACAGATCATCTTGGA 2230        2240        2250        2260        2270        2280
               •           •           •           •           •           •
      ACTGCATTCTTCTGAGCACTGTTTATACACTGTGTAAATACCCATATGTCCTGAATTC
```

METHOD OF TREATMENT USING TIE2 LIGAND2

CROSS-REFERENCE TO RELATED APPLICATIONS

This application is a continuation of U.S. Ser. No. 10/186,817 filed 1 Jul. 2002 now abandoned, which is a continuation-in-part of U.S. Ser. No. 09/442,717 filed 18 Nov. 1999 now U.S. Pat. No. 6,627,415, which is a continuation of U.S. Ser. No. 08/930,721 filed 10 Mar. 1998, now abandoned, which is a National Stage Application of International Application PCT US96/04806 filed 5 Apr. 1996, now abandoned, the contents of each of which are hereby incorporated by reference.

BACKGROUND

1. Field of the Invention

The present invention is directed to tyrosine kinase with Ig and EGF homology domains ("TIE")-2 ligands, as well as to methods of making and using the TIE-2 ligands.

2. Description of Related Art

A gene encoding an endothelial cell transmembrane tyrosine kinase, originally identified by RT-PCR as an unknown tyrosine kinase-homologous cDNA fragment from human leukemia cells, was described by Partanen et al. (1990) Proc. Natl. Acad. Sci. USA, 87: 8913-8917. This gene and its encoded protein are called "TIE" which is an abbreviation for "tyrosine kinase with Ig and EGF homology domains." Partanen et al. (1992) Mol. Cell. Biol. 12: 1698-1707.

Two structurally related rat TIE receptor proteins have been reported to be encoded by distinct genes with related profiles of expression. One gene, termed tie-1, is the rat homolog of human tie. Maisonpierre et al. (1993) Oncogene 8: 1631-1637. The other gene, tie-2, may be the rat homolog of the murine tek gene, which, like tie, has been reported to be expressed in the mouse exclusively in endothelial cells and their presumptive progenitors. Dumont, et al. Oncogene 8: 1293-1301 (1993). The human homolog of tie-2 is described in U.S. Pat. No. 5,447,860.

BRIEF SUMMARY OF THE INVENTION

The present invention provides for a composition comprising a TIE-2 ligand substantially free of other proteins. The invention also provides for an isolated nucleic acid molecule encoding a TIE-2 ligand. The isolated nucleic acid may be DNA, cDNA or RNA. The invention also provides for a vector comprising an isolated nucleic acid molecule encoding a TIE-2 ligand. The invention further provides for a host-vector system for the production in a suitable host cell of a polypeptide having the biological activity of a TIE-2 ligand. The suitable host cell may be bacterial, yeast, insect or mammalian. The invention also provides for a method of producing a polypeptide having the biological activity of a TIE-2 ligand which comprises growing cells of the host-vector system under conditions permitting production of the polypeptide and recovering the polypeptide so produced.

The invention herein described of an isolated nucleic acid molecule encoding a TIE-2 ligand further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds a TIE-2 ligand. The antibody may be monoclonal or polyclonal. Thus the invention further provides for therapeutic compositions comprising an antibody which specifically binds a TIE-2 ligand in a pharmaceutically acceptable vehicle. The invention also provides for a method of blocking blood vessel growth in a mammal by administering an effective amount of a therapeutic composition comprising an antibody which specifically binds a TIE-2 ligand in a pharmaceutically acceptable vehicle.

The invention further provides for therapeutic compositions comprising a TIE-2 ligand in a pharmaceutically acceptable vehicle. The invention also provides for a method of promoting neovascularization in a patient by administering an effective amount of a therapeutic composition comprising a TIE-2 ligand in a pharmaceutically acceptable vehicle. In one embodiment, the method may be used to promote wound healing. In another embodiment, the method may be used to treat ischemia. In yet another embodiment, a TIE-2 ligand is used, alone or in combination with other hematopoietic factors, to promote the proliferation or differentiation of hematopoietic stem cells, B cells or megakaryocytic cells.

The invention also provides for a TIE-2 receptor antagonist as well as a method of inhibiting TIE-2 ligand biological activity in a mammal comprising administering to the mammal an effective amount of a TIE-2 antagonist. According to the invention, the antagonist may be the TIE-2 ligand 2 as described herein, an antibody or other molecule capable of specifically binding either TIE-2 ligand 1 or TIE-2 receptor (such as for example TIE-2 receptorbody), or ligandbody comprising the fibrinogen-like domain of TIE-2 ligand 1 or ligand 2.

Throughout this specification the TIE ligands are variously referred to. As used herein, TIE ligand 1=TL1=Angiopoietin-1=Ang1 and TIE ligand 2=TL2=Angiopoietin-2=Ang2.

One preferred embodiment of the invention is a method of reducing pathological neovascularization in a human comprising administering to the human an agent capable of interfering with Ang2-mediated biological effects such that pathological neovascularization is reduced. Another preferred embodiment is a method wherein the pathological neovascularization is ocular neovascularization, in particular wherein the pathological ocular neovascularization is proliferative retinopathy, such as diabetic retinopathy, ischemic retinopathy, or retinopathy of prematurity; choroidal neovascularization; lens neovasculation; corneal neovascularization; iridial neovascularization; or conjunctival neovascularization. Yet another preferred embodiment is a method of reducing the risk of retinal detachment associated with pathological ocular neovascularization in a human comprising administering to the human an agent capable of interfering with Ang2-mediated biological effects such that retinal detachment associated with pathological ocular neovascularization is reduced.

Also preferred are methods wherein the administration is topical, retrobulbar, subconjunctival, oral, subcutaneous, intraocular, intravitreal, subretinal, intramuscular, intranasal, intrathecal, intraarterial, intravenous, transvaginal, transdermal, or transanal administration.

Still another preferred embodiment is a method wherein the pathological neovascularization is tumor neovascularization, and in particular wherein the tumor is a solid tumor.

Preferred embodiments of the invention are ones in which the biological effects are Ang2-mediated cell signaling, Ang2 binding to Tie1, Ang2 binding to Tie2, or Ang2 antagonism of Ang1.

Also preferred are methods wherein the agent is capable of interfering with Ang2 binding to Tie1 or Tie2; is capable of interfering with Ang2-mediated cell signaling; or is capable of antagonizing Ang1 binding to Tie1 or Tie2.

BRIEF DESCRIPTION OF THE FIGURES

FIG. 2A-2B. Nucleic acid (SEQ ID NO:5) and deduced amino acid (single letter code) sequences (SEQ ID NO:6) of human TIE-2 ligand 2 from clone pBluescrip KS encoding human TIE 2 ligand 2.

DETAILED DESCRIPTION OF THE INVENTION

Figure 1:
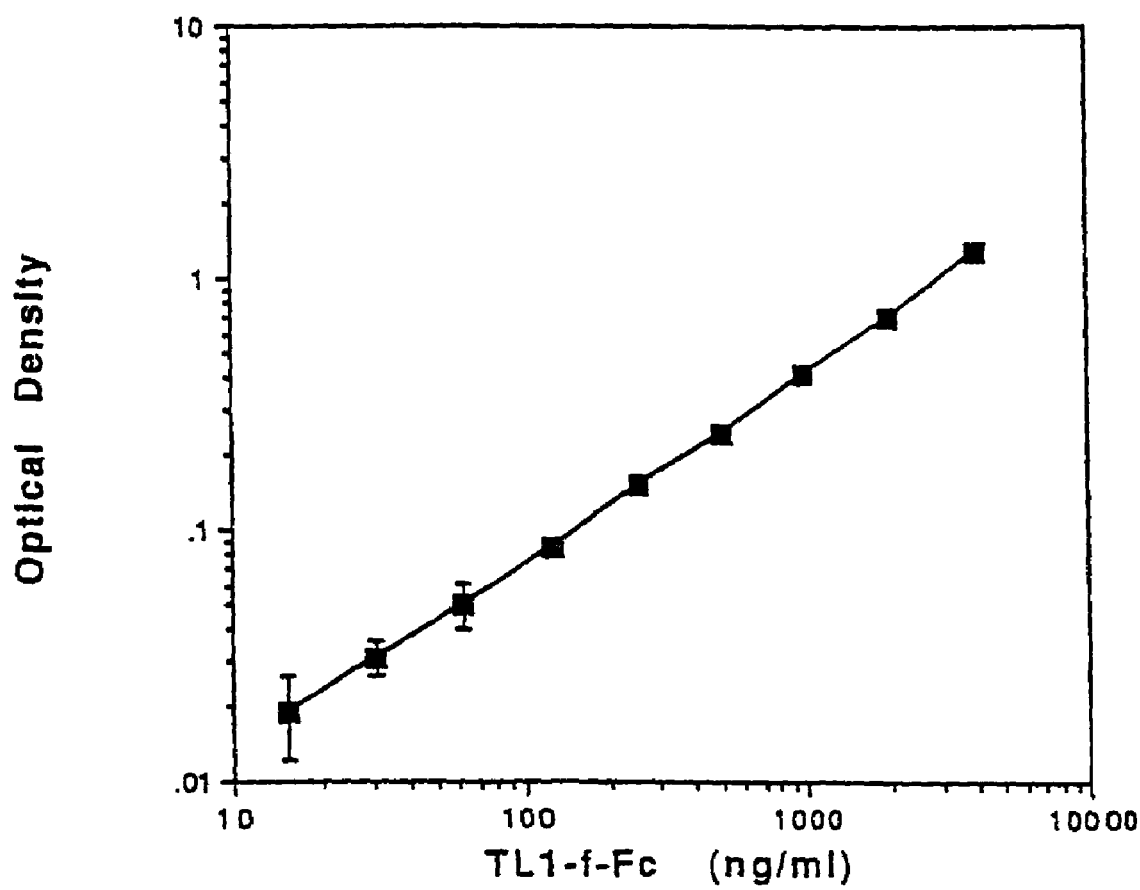
FIG. 1. A typical curve showing TIE-2 ligand 1 ligand-body comprising the fibrinogen-like domain of the ligand bound to the Fc domain of IgG (TL1-fFc) binding to immobilized TIE-2 ectodomain in a quantitative cell-free binding assay.

As described in greater detail below, applicants have isolated and identified novel ligands that bind the TIE-2 receptor. The TIE-2 ligands of the present invention, which may be purified from nature, or made recombinantly, are referred to herein as TIE-2 ligand 1 (or TL1 or Ang1) and TIE-2 ligand 2 (or TL2 or Ang2). TIE-2 ligand 1, which has an amino acid sequence (SEQ ID NO:2 or 4) which is encoded, inter alia, by the nucleic acid of SEQ ID NO:1 or 3, is a TIE-2 receptor agonist. TIE-2 ligand 2, which has an amino acid sequence (SEQ ID NO:6) which is encoded, inter alia, by the nucleic acid of SEQ ID NO:5, is a TIE-2 receptor antagonist.

The present invention comprises these TIE-2 ligands, as defined by their amino acid sequences, as well as functionally equivalent variants thereof comprising naturally occurring allelic variations, as well as proteins or peptides comprising substitutions, deletions or insertional mutants of the described sequences, which bind the TIE-2 receptors and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity as the TIE-2 ligands described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g. *E. coli*) expression systems. Functional equivalents also include mutants in which amino acid substitutions are made for cysteine molecules to improve stability of the molecules and to prevent unwanted crosslinking. As used herein, the term "TIE-2 ligand" also include fragments of the TIE-2 ligands which are associated with the binding of the ligands to the TIE-2 receptor. In a preferred embodiment, the TIE-2 ligand comprises the fibrinogen-like domain of TIE-2 ligands 1 and 2 as described herein.

The present invention also encompasses the nucleotide sequence that encodes the proteins described herein as TIE-2 ligands 1 and 2, as well as host cells, including yeast, bacteria, viruses, and mammalian cells, which are genetically engineered to produce the protein, by e.g. transfection, transduction, infection, electroporation, or microinjection of nucleic acid encoding the TIE-2 ligands described herein in a suitable expression vector. The present invention also encompasses introduction of the nucleic acids encoding TIE-2 ligands through gene therapy techniques such as is described, for example, in Finkel and Epstein (1995) FASEB J. 9:843-851; Guzman et al. (1994) Proc. Natl. Acad. Sci. (USA) 91:10732-10736.

One skilled in the art will also recognize that the present invention encompasses DNA and RNA sequences that hybridize to a deduced TIE-2 ligand encoding sequence, under conditions of moderate stringency, as defined in, for example, Sambrook et al. (1989) Molecular Cloning: A Laboratory Manual, 2 ed. Vol. 1, pp. 101-104, Cold Spring Harbor Laboratory Press. Thus, a nucleic acid molecule contemplated by the invention includes one having a sequence deduced from an amino acid sequence of a TIE-2 ligand prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds the TIE-2 receptor and which has an amino acid sequence and other primary, secondary and tertiary characteristics that are sufficiently duplicative of the ligands described herein so as to confer on the molecule the same biological activity as one of the TIE-2 ligands described herein.

In one embodiment, the biologically active form of the TIE-2 ligand is one in which the ligand is capable of binding the TIE-1 receptor. Preliminary data indicates that TL 2 binds TIE-1 receptor (albeit with low affinity) raising the possibility that it may be able to bind and activate the receptor, or, as in the case of the TIE-2 receptor, bind and act as antagonist.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE-2 ligand encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a TIE-2 ligand gene product, for example, by binding of the ligand to the TIE-2 receptor or portion thereof which may be tagged with, for example, a detectable antibody or portion thereof or by binding to antibodies produced against the TIE-2 ligand protein or a portion thereof. Cells of the present invention may transiently or, preferably, constitutively and permanently express TIE-2 ligands as described herein. In the fourth approach, DNA nucleotide primers can be prepared corresponding to a tie-2 specific DNA sequence. These primers could then be used to PCR a tie-2 gene fragment. (PCR Protocols: A Guide To Methods and Applications (1990) Edited by Michael A. Innis et al., Academic Press).

The recombinant ligands may be purified by any technique which allows for the subsequent formation of a stable, biologically active protein. Preferably, the ligands are secreted into the culture medium from which they are recovered. Alternatively, the ligand may be recovered from cells either as soluble proteins or as inclusion bodies, from which they may be extracted quantitatively by 8M guanidinium hydrochloride and dialysis in accordance with well known methodology. In order to further purify the ligand, affinity chromatography, conventional ion exchange chromatography, hydrophobic interaction chromatography, reverse phase chromatography or gel filtration may be used.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Also included are single chain Fvs. A single chain Fv (scFv) is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907 assigned to Cambridge Antibody Technology Limited incorporated by reference herein. Antibody molecules may be purified by known techniques, e.g., immunoabsorption or immunoaffinity chromatography, chromatographic methods such as HPLC (high performance liquid chromatography), or a combination thereof.

In addition, the invention further contemplates compositions wherein the TIE-2 ligand is the receptor binding domains of the TIE-2 ligands described herein. For example, TIE-2 ligand 1 consists of a "coiled coil" domain (beginning at the 5' end and extending to the nucleotide at about position 1160 of SEQ ID NO:1 and about position 1157 of SEQ ID NO:3) and a fibrinogen-like domain (which is encoded by the nucleotide sequence of SEQ ID NO:1 beginning at about position 1161 and about position 1158 of SEQ ID NO:3). The fibrinogen-like domain of TIE-2 ligand 2 is believed to begin on or around the same amino acid sequence as in ligand 1 (FRDCA) which is encoded by nucleotides beginning around 1197 of SEQ ID NO:5. Multimerization of the coiled coil domains during production of the ligand hampers purification. Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti-myc antibodies, do bind the TIE-2 receptor (clustered ligands and ligandbodies are described in Davis et al. (1994) Science 266:816-819). Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of TIE-2 ligandbodies which may be used as targeting agents, in diagnostics or in therapeutic applications, such as targeting agents for tumors and/or associated vasculature wherein a TIE-2 antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE-2 receptor. Such molecules may be used in a method of treatment of the human or animal body, or in a method of diagnosis.

Because TIE-2 receptor has been identified in association with endothelial cells and, as demonstrated herein, blocking of TIE-2 ligand 1 appears to prevent vascularization, applicants have demonstrated that the TIE-2 ligand 1 will be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic. Ferrara, et al. U.S. Pat. No. 5,332,671, which describes in vitro and in vivo studies that may be used to demonstrate the effect of an angiogenic factor in enhancing blood flow to ischemic myocardium, enhancing wound healing, and in other therapeutic settings wherein neoangiogenesis is desired (see EP 0 550 296 A2; Banai et al. (1994) Circulation 89:2183-2189; Unger et al. (1994) Am. J. Physiol. 266: H1588-H1595; Lazarous et al. (1995) Circulation 91:145-153). According to the invention, the TIE-2 ligands may be used alone or in combination with one or more additional pharmaceutically active compounds such as, for example, VEGF or basic fibroblast growth factor (bFGF), as well as cytokines, neurotrophins, etc.

Conversely, antagonists of the TIE-2 receptor, such as receptorbodies as described herein, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. The TIE-2 ligands described herein may also be used in combination with agents, such as cytokine antagonists such as IL-6 antagonists, that are known to block inflammation.

For example, applicants have determined that the TIE-2 ligands are expressed in cells within, or closely associated with, tumors. TIE-2 ligand 2 appears to be tightly associated with tumor endothelial cells. Accordingly, TIE-2 antagonists, such as TIE-2 ligand 2 or TIE-2 ligandbodies may also be useful in preventing or attenuating, for example, tumor growth. In addition, TIE-2 ligands or ligandbodies may be useful for the delivery of toxins to a receptor bearing cell. Alternatively, other molecules, such as growth factors, cytokines or nutrients, may be delivered to a TIE-2 receptor bearing cell via TIE-2 ligands or ligandbodies. TIE-2 ligands or ligandbodies could also be used as a diagnostic reagent for the TIE-2 receptor, to detect the receptor in vivo or in vitro. Where the TIE-2 receptor is associated with a disease state, TIE-2 ligands or ligandbodies may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in WO 95/26364 and Burrows et al. (1993) Proc. Natl. Acad. Sci. USA 90:8996-9000 which is incorporated herein in its entirety.

In other embodiments, the TIE-2 ligands described herein are used as hematopoietic factors. A variety of hematopoietic factors and their receptors are involved in the proliferation and/or differentiation and/or migration of the various cells types contained within blood. Because the TIE-2 receptors are expressed in early hematopoietic cells, the TIE-2 ligands are expected to play a comparable role in the proliferation or differentiation or migration of these cells. Thus, for example, TIE-2 containing compositions may be prepared, assayed, examined in vitro and in vivo biological systems and used therapeutically.

The TIE-2 ligands of the present invention may be used alone, or in combination with another pharmaceutically active agent such as, for example, cytokines, neurotrophins, interleukins, etc. In a preferred embodiment, the ligands may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE-2 receptor antagonists, such as TL2, are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the TIE-2 ligand 2, TIE-2 antibody, TIE-2 receptorbody, a conjugate of a TIE-2 ligand or a ligandbody or fFC as described herein.

The present invention also provides for pharmaceutical compositions comprising the TIE-2 ligands or ligandbodies described herein, peptide fragments thereof, or derivatives in a pharmacologically acceptable vehicle. The TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The invention further provides for a therapeutic composition comprising a human TIE-2 ligand or ligandbody and a cytotoxic agent conjugated thereto. In one embodiment, the cytotoxic agent may be a radioisotope or toxin.

The invention also provides for a therapeutic composition comprising a human TIE-2 ligand or ligandbody in a pharmaceutically acceptable vehicle, as well as a method of promoting neovascularization in a patient comprising administering to the patient an effective amount of the therapeutic composition.

In a specific embodiment of the present invention, methods and compositions are provided for the treatment of ocular neovascularization including proliferative retinopathies characterized by pre-retinal or optic disc neovascularization, such as diabetic retinopathy, venous obstructive disease, ocular ischemic syndrome, retinopathy of prematurity, hemoglobinopathies (e.g. sickle cell anemia), radiation retinopathy, ocular inflammation or infection, ocular neoplasias, tumors and metastases, ocular trauma or injury, or ocular neovascularization occurring idiopathically. In another specific embodiment of the present invention, methods and compositions are provided for the treatment of choroidal neovascularization disorders and diseases characterized by abnormal growth of new vessels, that originate in the choroid, penetrate Bruch's membrane and proliferate beneath the retinal pigment epithelium and/or neural retina, including, age related macular degeneration, angiod streaks, radiation retinopathy, ocular inflammation or infection, ocular neoplasias, tumors and metastases, ocular trauma or injury, or those occurring idiopathically, and other pathological conditions, in a subject in need of such treatment. The subject is typically a mammal, and most preferably a human. Diagnosis of ocular neovascularization is known by those skilled in the art.

The methods of the invention comprise administering a therapeutically effective amount of pharmaceutical compositions comprising agents capable of interfering with Ang2-mediated biological effects, in an acceptable pharmaceutical carrier to a subject in need, i.e., a subject afflicted with ocular neovascularization. Suitable agents capable of interfering with Ang2-mediated biological effects include, but are not limited to, any agent capable of preventing Ang2 expression, such as anti-sense molecules, or any agent capable of blocking Ang2 interaction with the Tie1 or Tie2 receptor, or any agent capable of interfering with Ang2-mediated biological effects including but not limited to cell signaling. Suitable agents capable of blocking such interaction between Ang2 and Tie 1 or Tie2 include antibodies, including monoclonal antibodies, directed against either Tie 1, Tie2, or Ang2. Skilled artisans will readily recognize that suitable anti-Tie2 or anti-Tie 1 antibodies include blocking antibodies, whereas suitable anti-Ang2 antibodies include neutralizing antibodies. In addition, fragments of antibodies, including scFvs and molecules containing scFvs, are also suitable for use in interfering with Ang2-mediated biological effects. Such scFvs or other antibody fragments may be derived from either anti-Ang2, anti-Tie1, or anti-Tie2 antibodies, and may be used alone or in combination with each other or other agents. Other agents capable of interfering with Ang2-mediated biological effects include receptor bodies that contain the extracellular domain of either Tie1 or Tie2 fused to the constant or Fc domain of an IgG. Specifically, Tie1 or Tie2 receptor bodies are suitable agents for blocking and inhibiting Ang2-mediated biological effects. Other suitable agents are small molecules, lipids, proteins, carbohydrates, or other organic or inorganic molecules capable of interfering with Ang2-mediated biological effects. Such molecules may act to bind to the Tie2 receptor, thus preventing Ang2 binding, or they may prevent or limit or otherwise alter Tie1 or Tie2 receptor signaling subsequent to Ang2 binding. Also suitable are small molecules, lipids, proteins, carbohydrates, or other organic or inorganic molecules that bind to or interact with Ang2 directly, thus preventing, inhibiting or limiting Ang2's ability to bind to the Tie2 receptor.

The agents may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active agents into preparations which can be used pharmaceutically. Proper formulation is dependent upon the route of administration chosen.

For topical administration the compounds may be formulated as solutions, gels, ointments, creams, suspensions, etc. as are well-known in the art.

Systemic formulations include those designed for administration by injection, e.g. subcutaneous, intraocular, intravenous, intramuscular, intrathecal or intraperitoneal injection, as well as those designed for transdermal, transmucosal, oral or pulmonary administration. For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active agents with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the agents of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

In preferred embodiments, the agents are prepared as a lyophilized powder that is to be reconstituted with sterile water for injection at appropriate concentrations. The reconstituted solution is buffered at an appropriate pH, typically neutral. In the preferred embodiment, the agents contain no preservative.

The agents will generally be used in an amount effective to achieve the intended purpose, i.e., treating ocular neovascularization. For use to treat ocular neovascularization, the agents, or pharmaceutical compositions thereof, are administered or applied in a therapeutically effective amount. By therapeutically effective amount is meant an amount effective to ameliorate or prevent the symptoms or conditions of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms are detectable or even when they are not detectable. The therapy may be provided alone or in combination with other drugs.

EXAMPLES

Example 1

Identification of the ABAE Cell Line as Reporter Cells for the TIE-2 Receptor

Adult BAE cells are registered in the European Cell Culture Repository, under ECACC#92010601. (See (1978) Proc. Natl. Acad. Sci. 75:2621). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at 14,000×G for 10 minutes, at 4° C. and the supernatants were subjected to immunoprecipitation with antisera specific for TIE-2 receptor, with or without the presence of blocking peptides added to ~20 g/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

Example 2

Cloning and Expression of TIE-2 Receptorbody for Affinity-Based Study of the TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin et al. (1993) Cell 73:447-456.

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-NotI fragment into the baculovirus transfer plasmid pVL1393. Plasmid DNA purified by cesium chloride density gradient centrifugation was recombined into viral DNA by mixing 3 g of plasmid DNA with 0.5 g of Baculo-Gold DNA (Pharminigen), followed by introduction into liposomes using 30 g Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly et al. (1992) *Baculovirus Expression Vectors—A Laboratory Manual*. 1992, New York: W. H. Freeman) except that the agarose overlay contained 125 g/mL X-gal (5-bromo-4-chloro-3-indolyl- -D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 g/mL MTT (3-[4,5-dimethylthiazol-2-yl]2, 5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1×antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10$^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 m, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 receptorbody were pooled and dialyzed versus PBS.

Example 3

TIE-2 Has a Critical Role in Development of the Vasculature

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al. (1993) Oncogene 8:3277-3288. Each Gelfoam piece absorbed approximately 6 μg of protein in 30 μl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1. Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2-5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

Example 4

Identification of a TIE-2-Specific Binding Activity in Conditioned Medium from the ras Oncogene-Transformed C2C12 Mouse Myoblast Cell Line Screening of ten-fold-concentrated cell-conditioned media (10×CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras-), RAT 2-ras (which is a ras transformed fibroblast cell line), human glioblastoma T98G and the human neuroblastoma cell line known as SHEP-1.

The C2C12-ras-10×CCM originated from a stably transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin/streptomycin supplemented with 10% fetal calf serum (FCS). Serum-free C2C12-ras-10×CCM was made by plating the cells at 60% confluence in a serum free defined media for 12 hours. [Zhan and Goldfarb, Mol. Cell. Biol. 6: 3541-3544 (1986)); Zhan, et al. Oncogene 1: 369-376 (1987)]. The medium was discarded and replaced with fresh DMEM/Q/P-S for 24 hours. This medium was harvested and cells were re-fed fresh DMEM/Q/P-S, which was also harvested after a further 24 hours. These CCM were supplemented with the protease inhibitors PMSF (1 mM) and aprotinin (10 g/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10×CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade-sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). A negative control surface of the EHK-1 receptorbody was prepared in a similar manner.

The running buffer used in the system was HBS (10 mM Hepes, 3.4 mM EDTA, 150 mM NaCl, 0.005% P20 surfactant, pH 7.4). The 10×CCM samples were centrifuged for 15 min at 4° C. and further clarified using a sterile, low protein-binding 0.45 µm filter (Millipore; Bedford, Mass.). Dextran (2 mg/ml) and P20 surfactant (0.005%) were added to each CCM sample. Aliquots of 40 µL were injected across the immobilized surface (either TIE-2 or EHK-1) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-µL pulse of 3 M $MgCl_2$.

The instrument noise level is 20 RU; therefore, any binding activity with a signal above 20 RU may be interpreted as a real interaction with the receptor. For C2C12-ras-conditioned media, the binding activities were in the range 60-90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50×concentrated C2C12-ras- CCM resulted in a four-fold enhancement over background of the TIE-2 specific binding signal.

Example 5

C2C12-ras- CCM Contains an Activity that Induces Tyrosine Phosphorylation of TIE-2 Receptor C2C12-ras-10×CCM was examined for its ability to induce tyrosine phosphorylation of TIE-2 in ABAE cells. Serum-starved ABAE cells were briefly incubated with C2C12-ras- CCM, lysed and subjected to immunoprecipitation and Western analyses as described above. Stimulation of serum-starved ABAE cells with serum-free C2C12-ras-10×CCM was done as follows. The medium of ABAE cells starved as described above was removed and replaced with either defined medium or 10×CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras- CCM stimulated at least a 100× increase in TIE-2 phosphorylation. This activity was almost totally depleted by pre-incubation of the C2C12-ras-10×CCM for 90 minutes at room temperature with 13 µg of TIE-2 RB coupled to protein G-Sepharose beads. Medium incubated with protein G Sepharose alone was not depleted of this phosphorylating activity.

Example 6

Expression Cloning of TIE-2 Ligand

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector is a modified version of the vector pSR (Takebe, et al. 1988, Mol. Cell. Biol. 8:466-472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3-4 hours at 37° C. in an atmosphere of 5% $CO_2$. The transfection media was aspirated and replaced with PBS with 10% DMSO for 2-3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15-30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody (RB), which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2 RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30-60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

Example 7

Isolation and Sequencing of the Human TIE-2 Ligand

A human fetal lung cDNA library in lambda gt-10 was obtained from Clontech Laboratories, Inc. (Palo Alto, Calif.). Plaques were plated at a density of $1.25 \times 10^6/20 \times 20$ cm plate, and replica filters taken following standard procedures (Sambrook et al., (1989) supra).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5 \times 10^8$ cpm/ng. Hybridization was carried out at 65° C. in hybridization solution containing 0.5 mg/ml salmon sperm DNA. The filters were washed at 65° C. in 2×SSC, 0.1% SDS and exposed to Kodak XAR-5 film overnight at −70° C. Positive phage were plaque purified. High titer phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463-5467).

Subcloning of the human tie-2 ligand DNA into a mammalian expression vector may be accomplished as follows. The clone λgt10 encoding htie-2 ligand 1 contains an EcoRI site located 490 base pairs downstream from the start of the coding sequence for the human TIE-2 ligand. The coding region may be excised using unique restriction sites upstream and downstream of the initiator and stop codons respectively. For example, an SpeI site, located 70 bp 5' to the initiator codon, and a Bpu1102i (also known as Blpl) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpul 102i sites are both made blunt ended). The coding region from the clone λgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone λgt10 encoding htie-2 ligand 1 is shown in SEQ ID NO:1.

In addition, full length human tie-2 ligand cDNA clones were obtained by screening a human glioblastoma T98G cDNA library in the pJFE14 vector. Clones encoding human TIE-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone λgt10 encoding htie-2 ligand 1. As shown in SEQ ID NO:1, the clone λgt10 encoding htie-2 ligand 1 contains an additional glycine residue which is encoded by nucleotides 1114-1116. The coding sequence of the T98G clone does not contain this glycine residue but otherwise is identical to the coding sequence of the clone λgt10 encoding htie-2 ligand 1. SEQ ID NO:3 sets forth the nucleotide and deduced amino acid sequence of human TIE-2 ligand from the T98G clone.

Example 8

Isolation and Sequencing of Second Human TIE-2 Ligand

A human fetal lung cDNA library in lambda gt-10 was obtained from Clontech Laboratories, Inc. (Palo Alto, Calif.). Plaques were plated at a density of $1.25 \times 10^6/20 \times 20$ cm plate, and replica filters taken following standard procedures (Sambrook, et al. (1989) supra). Duplicate filters were screened at low stringency (2×SSC, 55° C.) with probes made to the human TIE-2 ligand 1 sequence. One of the duplicate filters was probed with a 5' probe, encoding amino acids 25-265 of human TIE-2 ligand 1 as set forth in SEQ ID NO:1. The second duplicate filter was probed with a 3' probe, encoding amino acids 282-498 of human TIE-2 ligand 1 sequence. Both probes were hybridized at 55° C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse TIE-2 ligand 1 (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3-4 hours at 37° C. in an atmosphere of 5% $CO_2$. The transfection media was aspirated and replaced with phosphate-buffered saline with 10% DMSO for 2-3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells/100 mm plate. The cells were rinsed with PBS and then incubated with PBS containing 1.8% formaldehyde for 15-30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2 receptorbody. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30-60 min. The dish was then inspected microscopically for the presence of stained cells. Cells expressing one orientation of the clone, but not the other orientation, were seen to bind the TIE-2 receptorbody.

The coding region from the clone pBluescript KS encoding human TIE-2 ligand 2 was sequenced using the ABI 373A DNA sequencer and Taq Dideoxy Terminator Cycle Sequencing Kit. The nucleotide and deduced amino acid sequence of human TIE-2 ligand from the clone pBluescript KS encoding human TIE-2 ligand 2 is shown in SEQ ID NO:5.

Example 9

TIE-2 Ligand 2 as a Receptor Antagonist

Conditioned media from COS cells expressing either TIE-2 ligand 2 (TL2) or TIE-2 ligand 1 (TL1) were compared for their ability to activate TIE-2 receptors naturally present in human endothelial cell lines. Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman (1985) Proc. Natl. Acad. Sci. USA 82: 689-693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, as described in example 1. Phosphotyrosine levels on the TIE-2 receptor (TIE-2-R) were induced by treatment of HEAC cells with TIE-2 ligand 1 but not by TIE-2 ligand 2 conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Semi-confluent HAEC cells were serum-starved as described above and then incubated for 3 min., at 37° C. with 1-2 ml. of 20×COS/JFE14-TL2 conditioned medium. Control plates were treated with 20×COS/JFE14-only medium (MOCK). The plates were removed from the incubator and various dilutions of COS/JFE14-TL1 medium were then added, followed by further incubation of the plates for 5-7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20×COS/JFE14-TL1 medium diluted to 2×, 0.5×, 0.1×, or 0.02× by addition of 20×COS/JFE14-alone medium. An assay of the initial 20×TL1 and 20×TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot indicate that when compared to prior treatment of HAEC cells with MOCK medium, prior treatment of HAEC cells with excess TIE-2 ligand 2 antagonizes the subsequent ability of dilute TIE-2 ligand 1 to activate the TIE-2 receptor (TIE-2-R).

The ability of TL2 to competitively inhibit TL1 activation of the TIE-2-R was further demonstrated using the human cell hybrid line, EA.hy926 (see Example 21 for detailed description of this cell line and its maintenance). Experiments were performed in which unconcentrated COS cell media containing TL1 were mixed at varying dilutions with either MOCK- or TL2-conditioned media and placed on serum-starved EA.hy926 cell monolayers for 5 minutes at 37° C. The media were then removed, the cells were harvested by lysis and TIE-2-specific tyrosine phosphorylation was examined by Western blots, as described above. The results show that treatment of the EA.hy926 cells with 1×COS-TL1 alone robustly activated the endogenous TIE-2-R in these cells, whereas 1×TL2 COS medium was inactive. However, mixture of TL1 with either MOCK or TL2 demonstrated that TL2 can block the activity of TL1 in a dose-dependent fashion. In the central three pairs of lanes the ratio of TL2 was decreased while the amount of TL1 in the mixture was correspondingly increased from 0.1× to 0.3×. At any of these mixture ratios the TL1:TL2 lanes showed a reduced level of TIE-2-R phosphorylation compared to that of the corresponding TL1:MOCK lanes. When the amount TL1 was held steady and the amount of TL2 was decreased, however, a point was reached at which the TL2 in the sample was too dilute to effectively inhibit TL1 activity. The relative amount of each ligand present in these conditioned COS media could be estimated from their binding units as measured by the BIAcore assay and from Western blots of the COS media with ligand-specific antibodies. Consequently, we can infer that only a few-fold molar excess of TL2 is required to effectively block the activity of TL1 in vitro. This is significant because we have observed distinct examples in vivo (see Example 17) where TL2 mRNAs achieve considerable abundance relative to those of TL1. Thus, TL2 may be serving an important physiological role in effectively blocking signaling by the TIE-2-R at these sites.

Taken together these data confirm that, unlike TL1, TL2 is unable to stimulate endogenously expressed TIE-2-R on endothelial cells. Furthermore, at a few fold molar excess TL2 can block TL1 stimulation of the TIE-2 receptor, indicating that TL2 is a naturally occurring TIE-2 receptor antagonist.

Example 10

Identification of TIE-2-Specific Binding Activity in CM and Supernatants

Binding activity of 10×CCM from the cell lines C2C12-ras, Rat2 ras, SHEP, and T98G, or COS cell supernatants after transfection with either human TIE-2 ligand 1 (hTL1) or human TIE-2 ligand 2 (hTL2) was measured using biosensor technology (BIAcore; Pharmacia Biosensor, Piscataway, N.J.) which monitors biomolecular interactions in real-time via surface plasmon resonance (SPR). Purified rat or human TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). In general, 9000-10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 µm filter (Millipore; Bedford, Mass.). Dextran (2 mg/ml) and P20 surfactant (0.005%) were added to each sample. Aliquots of 40 µL were injected across the immobilized surface (either rat or human TIE-2) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-µL pulse of 3 M $MgCl_2$.

The CCM samples (C2C12-ras, Rat2-ras, SHEP, T98G) were tested on the rat TIE-2 RB immobilized surface, while the recombinant hTL1 and hTL2 were tested on the human TIE-2 RB immobilized surface. In each case, specific binding to the TIE-2 receptorbody was evaluated by incubating the samples with 25 µg/ml of either soluble TIE-2 (rat or human) RB or trkB RB prior to assaying the binding activity. The addition of soluble trkB RB causes a slight decrease in the TIE-2 binding activity, while the addition of soluble TIE-2 RB significantly reduces the binding activity as compared to that measured in the absence of TIE-2 RB.

Example 11

TIE-2 RB Blocks Activation of the TIE-2 Receptor by TIE-2 Ligand 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE-2- or TrkB-RB and then compared for their ability to activate TIE-2 receptors naturally present in a human endothelial cell line.

Conditioned COS media were generated from COS-7 cells transfected with either the pJFE14 expression vector alone, or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Northern (RNA) analyses revealed significant levels of tie-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE-2- or TrkB-RBs to COS media containing TL1. HUVEC cells were maintained at 37° C., 5% $CO_2$ in a complete endothelial cell growth medium (Clonetics, Inc.) that contained 5% fetal bovine serum, soluble bovine brain extract with 10 µg/ml heparin, 10 ng/ml human EGF, 1 µg/ml hydrocortisone, 50 µg/ml gentamicin and 50 ng/ml amphotericin-B. Assessment of whether TL1 could activate TIE-2 receptor in the HUVEC cells was done as follows. Confluent dishes of HUVEC cells were serum-starved for two-to-four hours in low-glucose Dulbecco's. MEM at 37° C., 5% $CO_2$, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE-2- or TrkB-RB added to 50 μg/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1. Phosphotyrosine levels on the TIE-2 receptor were induced by treatment of HUVEC cells with TIE-2 ligand 1 (TL1) relative to that seen with control medium and this induction is specifically blocked by prior incubation with TIE-2-RB (TIE-2-Fc) but not by incubation with TrkB-RB (TrkB-Fc). These data indicate that soluble TIE-2 RB can serve as a selective inhibitor to block activation of TIE-2 receptor by TIE-2 ligand 1.

Example 12

Construction of TIE-2 Ligandbodies

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TL2-Fc was cloned as an Eco RI-NotI fragment into the baculovirus transfer plasmid pVL1393. Plasmid DNA was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly et al. (1992) supra) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT (3-[4,5-dim-ethylthiazol-2-yl]2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1×antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10 6 cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTL2-Fc-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

Example 13

Expression of TIE-1, TIE-2, TL1, and TL2 in Renal Cell Carcinoma

In situ hybridization experiments were performed on human renal cell carcinoma tumor tissue using TIE-1, TIE-2, TL1, and TL2 cDNA probes. TIE-2, TIE-1, TL1, and TL2 expression were all up-regulated in the tumor vasculature. Ligand expression appeared to be localized to either the vascular endothelial cells (TL2) or very near the vascular endothelial cells in the mesenchyme (TL1). VEGF has been shown to be dramatically up-regulated in this tumor tissue. Brown, et al. Am. J. Pathol. 143:1255-1262 (1993).

Example 14

Expression of TIE-1, TIE-2, TL1, and TL2 in Wound Healing

In situ hybridization experiments were performed on cross-sectional tissue slices obtained from a rat cutaneous wound model using TIE-1, TIE-2, TL1, and TL2 cDNA probes. The wound healing model involves pressing a small cork bore against the skin of a rat and removing a small, cylindrical plug of skin. As healing begins at the base of the wound, a vertical slice of tissue is taken and used for in situ hybridization. In the tested tissue sample, TL1 and TL2 appeared to be slightly up-regulated by four days post-injury. In contrast to the slightly up-regulated expression of TL1 and TL2 in this tissue, VEGF expression, which may precede TL1 and TL2 expression, is dramatically up-regulated.

Example 15

Expression of TIE Ligands in Fetal Liver and Thymus

Reverse transcription-PCR (RT-PCR) was performed on mouse E14.5 fetal liver and mouse E17.5 fetal thymus. Agarose gel electrophoresis of the RT-PCR products revealed that in the mouse fetal liver, TIE-2 ligand 1 (TL1) RNA is enriched in the stromal region, but is absent in c-kit+TER119 hematopoietic precursor cells. In this same tissue, TIE-2 ligand 2 (TL2) RNA is enriched in the stromal cells, but absent in the hematopoietic precursor cells. In the mouse fetal thymus, TL2 is enriched in the stromal cells.

Example 16

The TIE Receptor/Ligand System in Angiogenesis

Although the TIE-2/TIE ligand system appears to play an important role in endothelial cell biology, it has not been shown to play a significant, active role in the early to intermediate stages of vascularization (e.g. angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (e.g. de-stabilization/de-differentiation of mature endothelial cells allowing the formation of new vessels from existing vasculature, inhibition of inappropriate blood vessel formation, and regression/involution of mature blood vessels).

Example 17

Expression of TIE Ligands in the Female Reproductive System (Ovary)

Preliminary observations made in experiments examining the expression of the TIE receptors and ligands in the female reproductive system are consistent with the hypothesis the TL1 plays a role in neovascularization which temporally follows that of VEGF. The pattern of TL2 expression is also consistent with an antagonism of the action of TL1, and a specific role in vascular regression. To verify this, expression of relevant mRNAs can be examined following experimental induction of follicular and luteal development so that their temporal relation to various aspects of neovascularization/vascular regression can be more clearly defined (e.g. in conjunction with endothelial cell staining, vascular fills). Angiogenesis associated with follicular development and corpus luteum formation in staged ovaries of mature, female rats or following induced ovulation in pre-pubertal animals was followed using in situ hybridization. These studies revealed that VEGF, TL1 and TL2 are expressed in a temporally and spatially coordinate fashion with respect to the development and regression of vasculature in the ovary,—specifically with respect to the establishment of the vascular system which is generated in the course of the conversion of an ovarian follicle to a corpus luteum (CL).

Briefly, VEGF expression increases in the follicular granule layer prior to its vascularization during the process of luteinization. During the process of CL formation, highest levels of VEGF expression are apparent in the center of the developing CL in the vicinity of luteinizing cells which are not yet vascularized. VEGF levels remain moderately high and are diffusely distributed in the developed CL. In contrast, noticeably enhanced expression of TIE-2 ligand 1 occurs only late in process of CL formation, after a primary vascular plexus has been established. Later, TL1 expression is apparent throughout the CL at which time the definitive capillary network of the CL has been established.

TL2 exhibits a more complex pattern of expression than either VEGF or TL1. In the developing CL, TL2 is expressed at highest levels at the front of the developing capillary plexus-between the central avascular region of the CL where VEGF expression is highest, and the most peripheral portion of the CL where TL1 expression is dominant and where the luteinization process is complete and the vascular system is most mature. TL2 also appears to be expressed at high levels in the follicular layer of large follicles which are undergoing atresia. While TL1 is also apparent in atretic follicles, VEGF is not expressed.

The pattern of expression described above is most consistent with a role for VEGF in the initiation of angiogenesis, with TL1 acting late in this process-for example in modeling and/or stabilization of the definitive vascular network. In contrast, TL2 is present both in areas of active expansion of a newly forming vascular network (during CL formation), and in regions which fail to establish a new vasculature and vascular regression is in progress (atretic follicles). This suggests a more dynamic and complex role for TL2, possibly involving destabilization of existing vasculature (necessary for regression) or developing vasculature (necessary for the dynamic modeling of newly forming vessels).

Example 18

Construction and Characterization of Cys-TL1 Mutant

The TIE-2 ligands have two major structural domains, one described as a "coiled-coil" domain comprising the approximate C-terminal third of the protein and the other a "fibrinogen-like" domain comprising the approximate N-terminal two-thirds of the protein. Although the TIE-2 ligands, designated TL1 and TL2, share similar structural homology, they exhibit different physical and biological properties. Under non-reducing electrophoretic conditions, both proteins exhibit covalent, multimeric structures, with TL1 existing primarily as a trimer and TL2 existing primarily as a dimer in terms of biological activity, TL1 has been shown to be an agonist of the TIE-2 receptor, as demonstrated by induction of phosphorylation in TIE-2 expressing cells. TL2, on the other hand, appears to be a competitive inhibitor of TL1. Investigations into what factors might be contributing to the different physical and biological properties of the two molecules revealed the presence of a cysteine residue (CYS265) preceding the fibrinogen-like domain in TL1 but absent in TL2. This CYS265 residue in TL1 is encoded by TGC and is located at about nucleotides 1102-1104 at the approximate junction between the coiled-coil and fibrinogen-like domains. Because cysteine residues are generally involved in disulfide bond formation, the presence of which can contribute to both the tertiary structure and biological properties of a molecule, it was thought the perhaps the presence of the CYS265 in TL1 might be at least partially responsible for the different properties of the two molecules. To test this hypothesis, an expression plasmid was constructed which contained a mutation in TL1 in which the CYS was replaced with an amino acid which does not form disulfide bonds. In addition to this TL1/CYS$^-$ mutant, a second expression plasmid was constructed which mutated the corresponding position in TL2 so that this residue was now a cysteine. Both non-mutated and mutated expression plasmids of TL1 and TL2 were transiently transfected into COS cells. Cell supernatants containing the recombinant proteins were harvested and samples subjected to both reducing and non-reducing SDS/PAGE electrophoresis and subsequent western blotting. Western blots of both non-mutated and mutated TL1 and TL2 proteins under revealing that the TL1/CYS$^-$ mutant behaves more TL2-like in that it runs as a dimer and that the TL2/CYS+ mutant behaves more TL1-like in that it is able to form a trimer as well as higher-order multimers. Interestingly, when the two mutant proteins were tested for their ability to induce phosphorylation in TIE-2 expressing cells, the TL1/CYS$^-$ mutant was able to activate the TIE-2 receptor, whereas the TL2/CYS$^+$ mutant did not gain any activating activity.

Example 19

Construction and Characterization of Fibrinogen-Like Domain Only Mutants

In order to test whether the fibrinogen-like domain (F-domain) of the TIE-2 ligands contained TIE-2 activating activity, expression plasmids were constructed which deleted the coiled-coil domain, leaving only that portion of the DNA sequence encoding the F-domain (beginning at about nucleotide 1159, amino acid residue ARG284). This mutant construct was transiently transfected into COS cells. The supernatant containing the recombinant protein was harvested. The TL1/F-domain mutant was tested for it's ability to bind the TIE-2 receptor. The results showed that, as a monomer, the TL1/F-domain mutant was not able to bind TIE-2 at a detectable level. However, when the TL1/F-domain monomer was myc-tagged and subsequently clustered with an antibody directed against the myc tag, it did exhibit detectable binding to TIE-2. However, the antibody-clustered TL1/F-domain mutant was not able to induce phosphorylation in a TIE-2 expressing cell line.

Example 20

Receptorbody Binding and a Ligand Binding/Competition Assay

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific anti-human Fc antibody which is alkaline phosphatase tagged. Excess reporter antibody is washed away, then the AP reaction is developed using a colored substrate. The assay is quantitated using a spectrophotometer. This assay has been used to evaluate the integrity of TIE-2-IgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 1 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

Example 21

EA.hy926 Cell Line as a Reporter Cell Line

EA.hy926 is a cell hybrid line that was established by fusion of HUVEC with the human lung carcinoma-derived line, A549 (Edgell, et al. (1983) Proc. Natl. Acad. Sci. (USA) 80, 3734-3737). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1× hypoxanthine-aminopterin-thymidine (HAT, Gibco/BRL). After three to four days of growth, the cells are passaged once again at $1.5 \times 10^6$ cells per T-75 flask and cultured an additional three to four days. For phosphorylation assays, cells prepared as described above were serum-starved by replacement of the culture medium with high-glucose DMEM and incubation for 2-3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 m M NaCl, 50 mM NaF, 1 mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

Example 22

Ang2 Role in Retinal Angiogenesis

Several studies suggest that embryonic vascular development is a coordinated collaboration between vascular endothelial cell growth factor (VEGF), VEGF receptor-1 (VEGFR1), VEGFR2, the Tie receptors, and their binding partners, Angiopoietin-1 (Ang1) and Ang2. A model has been proposed to explain observations made in mice with targeted disruption of genes. Acting through VEGFR2 (Flk1, KDR), VEGF stimulates differentiation of angioblasts into endothelial cells, and by activating VEGFR1 (Flt1), VEGF promotes assembly of endothelial cells into tubes. Ang1-induced activation of Tie2 results in remodeling, differentiation and stabilization of newly formed blood vessels, in part by promoting the appropriate association of endothelial cells with matrix and periendothelial support cells.

In addition to their effects on the embryonic vasculature, there is mounting evidence suggesting that Ang1 and Ang2 collaborate with VEGF during neovascularization at later stages of development and in adults. A survey of Ang 2 expression in adult tissues showed undetectable Ang2 mRNA levels in most tissues, but substantial levels in ovary, uterus, and placenta, three tissues in which physiologic angiogenesis occurs. There is a recurring cycle of vascular quiescence, followed by angiogenesis, and then vascular regression in corpus luteum and Ang2 levels were found to be low during quiescence and high during angiogenesis and regression, suggesting that Ang2 may play a role in both positive and negative vascular. Ang2 mRNA is also expressed at high levels in blood vessels associated with experimental and human glioblastoma. Interestingly, induction of Ang2 expression occurs rapidly following association of tumor cells with extant vessels. In the absence of appreciable VEGF expression, many of these blood vessels regress. As VEGF expression is increased as the tumor grows, angiogenesis is initiated in vessels that continue to express Ang2. The correlation between the initiation of angiogenesis and the coincident expression of Ang2 and VEGF has also been noted in other types of tumors, and in other conditions characterized by pathological neovascularization. These observations suggest that Ang2 participates with VEGF in vascular remodeling in situations other than embryonic vascular development.

Mice. Mice with a promoterless β-galactosidase gene replacing the translation initiation site and the signal peptide encoding sequences of the ang2 gene, resulting in disruption of the ang2 gene and expression of β-galactosidase under control of the ang2 promoter were generated using standard techniques familiar to the skilled artisan.

Murine model of oxygen-induced ischemic retinopathy. Ischemic retinopathy was produced as described by Smith et al., (1994) Invest. Ophthalmol. Vis. Sci., 35:101-111. Litters containing seven-day-old ang2 +/− (heterozygotes) and ang2 −/− (homozygous) mice were placed in an airtight incubator and exposed to an atmosphere of 75±3% oxygen for 5 days. Incubator temperature was maintained at 23±2° C., and oxygen was measured every 8 hours with an oxygen analyzer. After 5 days, the mice were removed from the incubator and sacrificed after various amounts of time in room air. Controls comprised ang2 +/− and ang2 −/− mice of the same age raised in room air.

Effects of Ana2 gene deletion on the development of retinal vasculature. At P10 and P18, ang2 −/− mice and littermate control ang2 +/− mice were perfused with fluorescein-labeled dextran and retinal flat mounts were prepared. In control mice and ang2 +/− mice, by P10, a dense vascular bed extended almost to the peripheral edge of the retina and there was no remaining hyaloid vasculature. In contrast, in P10 ang2 −/− mice, a substantial part of the peripheral retina was still avascular and in the posterior retina, the retinal capillaries were less dense than those in ang +/− mice. Also, the hyaloid vasculature was still present.

In both heterozygous and homozygous mice, retinal cross sections were double-labeled with biotinylated *Griffonia simplicifolia* lectin (GSA), which selectively stains vascular cells, and for LacZ, which identifies sites where the ang2 promoter is turned on. At P7, there were some remaining hyaloid vessels in ang2 +/− mice, but many more hyaloid vessels in ang2 −/− mice, and they stained intensely for LacZ. Ang2 −/− mice showed less GSA staining on the surface of the retina indicating fewer blood vessels, and the vessels that were present also showed LacZ labeling. At P10, there was complete regression of the hyaloid vasculature in ang2 +/− mice, but ang2 −/− mice still showed numerous hyaloid vessels that stained intensely for LacZ. Ang2 +/− mice showed a well-developed superficial capillary bed with penetrating vessels extending into the retina, while ang2 −/− mice showed no penetrating vessels. At P18 and P28, there were hyaloid vessels in ang2 −/−, but not in ang2 +/− mice, and the latter had a completely developed retinal vasculature with superficial, intermediate, and deep capillary beds, but the former had few vessels on the retinal surface and rare penetrating vessels with no intermediate or deep capillary beds. These data confirm the findings in retinal whole mounts and demonstrate that in the absence of Ang2, the hyaloid vessels fail to regress and there is incomplete development of the retinal vessels, particularly the deep capillary beds. The few vessels that were present within the retinas of some ang2 −/− mice indicate that while physiologic angiogenesis was markedly perturbed, it was not completely eliminated.

Effects of Ang2 gene deletion in oxygen-induced ischemic retinopathy. To investigate the effect of Ang2 deficiency on ischemia-induced retinal neovascularization, Applicants utilized the oxygen-induced ischemic retinopathy model. Briefly described, when wild type mice are placed in high oxygen at P7, some newly formed retinal vessels regress and then when the mice are placed in room air at P12, the retina is ischemic resulting in neovascularization by P17. When Ang2-deficient mice were placed in oxygen at P7, there was regression of the already sparse retinal vessels so that only a few retinal vessels remained. When the oxygen-treated Ang2-deficient mice were subsequently placed in room air, there was no retinal neovascularization. A cross-section through the midperipheral retina of a mouse exposed to high oxygen from P7 through P12 compared to the retina of an Ang2-deficient mouse that was never exposed to high oxygen shows little GSA staining indicating few retinal vessels and no neovascularization. A corresponding section from the unexposed Ang2-deficient mouse shows more retinal vessels within the retina. In both types of mice, the far periphery of the retina was avascular. A total of 3 oxygen-exposed Ang2-deficient mice were examined and they all showed no retinal neovascularization despite what must have been very ischemic retina due to few retinal blood vessels. They also showed persistence of the hyaloid vasculature.

Discussion. Mice deficient in Ang2 show abnormal postnatal vascular remodeling, which in the eye is manifested by lack of regression of the hyaloid vasculature and incomplete development of the retinal vasculature. In this study, Applicants have shown that the abnormal retinal vascular development consists of some formation of the superficial capillary bed, but almost complete lack of vessel penetration into the retina resulting in absence of the intermediate and deep capillary beds. In addition, Ang2-deficient mice fail to develop ischemia-induced retinal neovascularization.

Applicants' previous expression data are consistent with this interpretation. Expression of ang2 mRNA in the retina is low between P0 and P7 when the superficial capillary bed is developing and peaks on P8 when sprouting from the superficial capillaries occurs to form the deep capillary bed (Hackett et al., (2000) J. Cell. Physiol., 184:275-284). Also, ischemia results in enhanced retinal expression of ang2 mRNA.

Ang2 binds to Tie2, but does not typically stimulate phosphorylation and thereby acts as a natural, context-specific antagonist of Tie2. Transgenic mice that overexpress Ang2 have a phenotype similar to both Tie2-deficient and Ang1-deficient mice in which blood vessels form, but fail to mature properly. In the corpus luteum of the ovary there is a cycle of quiescence, vascular growth, and vascular regression. During quiescence Ang2 and VEGF levels are low, during vascular growth Ang2 and VEGF levels are high, and during vascular regression, Ang2 levels are high and VEGF levels are low (Maisonpierre et al. (1997) Science 277:55-60). These findings led to the hypothesis that Ang2 collaborates with VEGF to help regulate vascular growth and regression. In the absence of Ang2, Tie2 signaling is intact and endothelial cells associate normally with their supporting cells and matrix, which makes them less responsive to soluble signals such as VEGF and thereby promotes quiescence. In the presence of Ang2, Tie2 signaling is blocked which perturbs these interactions making endothelial cells more responsive to and dependent upon VEGF or other soluble survival- and growth-promoting signals; in the presence of VEGF, vascular growth occurs, but in the absence of VEGF both soluble and matrix-derived survival signals are lacking and vascular regression occurs. This hypothesis is further supported by the present study, which demonstrates that normal regression of the hyaloid vasculature, and both physiologic and pathologic angiogenesis in the retina, require Ang2.

Conclusion. It has been demonstrated that the temporal and spatial expression of Ang2 in the retina is consistent with the hypothesis that it plays a role in physiologic and pathologic neovascularization in the retina (Hackett et al., (2000) J. Cell. Physiol., 184:275-284). Targeted disruption of the ang2 gene provides a powerful way to explore the functions of Ang2, and an initial study has demonstrated that Ang2-deficient mice show lack of regression of the hyaloid vasculature and very abnormal retinal vascular development. In this study, Applicants have extended those findings to demonstrate that in the absence of Ang2, retinal vasculogenesis remains at least partially in tact, but both physiologic and pathologic angiogenesis are severely perturbed.

Example 23

Ang2 Role in Two Forms of Ocular Neovascularization

Introduction. Mice deficient in Ang2 show lack of regression of the hyaloid vasculature and abnormal retinal vascular development. In this study, Ang2-deficient mice were used to more broadly explore the role of Ang2 in ocular neovascularization.

Materials and Methods. Ang2-deficient mice and littermate controls were compared in 2 models of ocular neovascularization: oxygen-induced ischemic retinopathy (OIR) and ectopic expression of VEGF in photoreceptors (rhoNEGF transgenic mice).

Oxygen-induced ischemic retinopathy. As described in detail above, in the OIR model, exposure of Ang2-deficient mice to high levels of oxygen resulted in partial regression of the already somewhat sparse retinal vessels. When these oxygen-exposed mice with few retinal vessels were moved to room air, there was no ischemia-induced retinal neovascularization, while littermate controls developed extensive retinal neovascularization.

Ectopic expression of VEGF in photoreceptors. Otherwise normal mice that carry a transgene expressing human VEGF regulated by the bovine rhodopsin promoter (V6) develop neovascular sprouts arising from the deep capillary bed which grow down into the subjacent photoreceptor layer, toward the subretinal space. Mice deficient in Ang2 were crossed with rhoNEGF transgenic mice. Subsequently, F1 ang +/– mice that carried a rho/VEGF transgene were crossed with ang +/– mice. At P21, wild type and ang +/– offspring that carried a rho/VEGF transgene exhibited extensive retinal neovascularization, while ang –/– mice that carried a rho/VEGF transgene had little evidence of neovascularization. Like wild-type mice that carry the rho/VEGF transgene, mice that are heterozygous for the ang2 mutation and rho/VEGF develop sprouts that appear as hyperfluorescent spots under low-power magnification of fluorescein-perfused flat-mounted retinas. The fine microvascular structure of the sprouts can be seen under higher power. In contrast, mice homozygous for the ang2 mutation and heterozygous for rho/VEGF develop only a limited deep capillary bed in the central retina, and the number of sprouts that develop is far less than in heterozygotes, even considering the decreased area of the deep capillary bed.

Conclusions. Mice deficient in Ang2 develop little or no ocular neovascularization in two different models of ocular neovascularization. These data suggest that Ang2 plays an important role in the development of pathologic neovascularization.

Clinical relevance. Ocular neovascularization is an extremely common clinical problem. Retinal neovascularization in patients with diabetic retinopathy accounts for the most common cause of new blindness in individuals younger than 60 in developed countries and choroidal neovascularization in patients with age-related macular degeneration accounts for the majority of severe vision loss in patients over 60. The data presented herein suggests that Ang2 and other components of the Tie2 signaling pathway provide molecular targets for development of new treatments for ocular neovascularization. As demonstrated, Ang2 collaborates with VEGF to promote neovascularization. Therefore, inhibiting or blocking Ang2 should be a viable treatment option for disorders characterized by ocular neovascularization. Non-limiting examples of ocular neovascularization disorders include proliferative retinopathies characterized by pre-retinal or optic disc neovascularization, such as diabetic retinopathy, venous obstructive disease, ocular ischemic syndrome, retinopathy of prematurity, hemoglobinopathies (e.g. sickle cell anemia), radiation retinopathy, ocular inflammation or infection, ocular neoplasias, tumors and metastases, ocular trauma or injury, or ocular neovascularization occurring idiopathically. Choroidal neovascularization disorders and diseases characterized by abnormal growth of new vessels, that originate in the choroids, penetrate Bruch's membrane and proliferate beneath the retinal pigment epithelium and/or neural retina, include, age related macular degeneration, angiod streaks, radiation retinopathy, ocular inflammation or infection, ocular neoplasias, tumors and metastases, ocular trauma or injury, or those occurring idiopathically.

Example 24

Effect of Ang2 on Neovascularization in Tumors

An experiment was performed in which Lewis lung carcinoma cells were implanted subcutaneously in adult Ang2 knockout (Ang2 −/−) mice. The experimental groups were as follows: two Ang2 knockout mice with tumors, two Ang2 heterozygous mice (Ang2 +/−), and two wildtype controls (Ang2 +/+). The tumors were allowed to grow for 2 ½ weeks and then observed qualitatively. The tumors in the Ang2 knockout mice appeared to be more than 50% smaller and less well vascularized as compared to the Ang2 heterozygotes and wild type controls. These data demonstrate that mice deficient in Ang2 exhibit significantly decreased neovascularization in tumors.

Conclusions. These findings support previous expression data suggesting that Ang2 is important in pathological neovascularization and that inhibiting Ang2-mediated biological effects such as those leading to pathological neovascularization could ameliorate tumor angiogenesis. The apparent role of Ang2 in such diverse types of pathological neovascularization clearly suggests the broad clinical applicability of treating patients with agents capable of interfering with Ang2-mediated biological effects. In addition to treating tumors and pathological ocular neovascularization disorders such as those described herein, any disorder characterized by pathological neovascularization would be amenable to such intervetion, including but not limited to disorders and diseases of the female reproductive tract such as endometriosis and polycystic ovary syndrome, would also be.

DEPOSITS

The following have been deposited with the American Type Culture Collection, 10801 University Boulevard, Manassas, Va. 20110-2209 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding TIE-2 receptorbody was deposited with the ATCC on Oct. 7, 1994 and designated as "vTIE-2 receptorbody" under ATCC Accession No. VR2484. A lambda phage vector containing human tie-2 ligand DNA was deposited with the ATCC on Oct. 26, 1994 and designated as gt10 encoding htie-2 ligand 1 under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963.

We claim:

1. A method of reducing ocular neovascularization in a human comprising administering to the human an agent capable of interfering with Tie2 ligand 2 binding to TIE1 or TIE2, such that ocular neovascularization is reduced, wherein the agent is a ligandbody comprising the fibrinogen-like domain of Tie2 ligand 2 beginning at position 281 to 496 of amino acid sequence of SEQ ID NO: 6 coupled to an Fc domain of IgG.

2. The method of claim 1, wherein the ocular neovascularization is proliferative retinopathy or choroidal neovascularization.

3. The method of claim 2, wherein the ocular neovascularization is lens neovascularization, corneal neovascularization, iridal neovascularization or conjunctival neovascularization.

* * * * *

SEQUENCE LISTING

<160> NUMBER OF SEQ ID NOS: 6

<210> SEQ ID NO 1
<211> LENGTH: 2149
<212> TYPE: DNA
<213> ORGANISM: Homo sapien

<400> SEQUENCE: 1

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300
ggcagtacaa tgacagtttt cctttccttt gctttcctcg ctgccattct gactcacata     360
gggtgcagca atcagcgccg aagtccagaa aacagtggga gaagatataa ccggattcaa     420
catgggcaat gtgcctacac tttcattctt ccagaacacg atggcaactg tcgtgagagt     480
acgacagacc agtacaacac aaacgctctg cagagagatg ctccacacgt ggaaccggat     540
ttctcttccc agaaacttca acatctggaa catgtgatgg aaaattatac tcagtggctg     600
```

-continued

```
caaaaacttg agaattacat tgtggaaaac atgaagtcgg agatggccca gatacagcag    660
aatgcagttc agaaccacac ggctaccatg ctggagatag aaccagcct cctctctcag    720
actgcagagc agaccagaaa gctgacagat gttgagaccc aggtactaaa tcaaacttct    780
cgacttgaga tacagctgct ggagaattca ttatccacct acaagctaga gaagcaactt    840
cttcaacaga caaatgaaat cttgaagatc catgaaaaaa acagtttatt agaacataaa    900
atcttagaaa tggaaggaaa acacaaggaa gagttggaca ccttaaagga agagaaagag    960
aaccttcaag gcttggttac tcgtcaaaca tatataatcc aggagctgga aaagcaatta   1020
aacagagcta ccaccaacaa cagtgtcctt cagaagcagc aactggagct gatggacaca   1080
gtccacaacc ttgtcaatct ttgcactaaa gaaggtgttt tactaaaggg aggaaaaaga   1140
gaggaagaga aaccatttag agactgtgca atgtatatc aagctggttt taataaaagt    1200
ggaatctaca ctatttatat taataatatg ccagaaccca aaaggtgtt ttgcaatatg    1260
gatgtcaatg ggggaggttg gactgtaata caacatcgtg aagatggaag tctagatttc   1320
caaagaggct ggaaggaata taaaatgggt tttggaaatc cctccggtga atattggctg   1380
gggaatgagt ttattttgc cattaccagt cagaggcagt acatgctaag aattgagtta    1440
atggactggg aagggaaccg agcctattca cagtatgaca gattccacat aggaaatgaa   1500
aagcaaaact ataggttgta tttaaaaggt cacactggga cagcaggaaa acagagcagc   1560
ctgatcttac acggtgctga tttcagcact aaagatgctg ataatgacaa ctgtatgtgc   1620
aaatgtgccc tcatgttaac aggaggatgg tggtttgatg cttgtggccc ctccaatcta   1680
aatggaatgt tctatactgc gggacaaaac catggaaaac tgaatgggat aaagtggcac   1740
tacttcaaag ggcccagtta ctccttacgt tccacaacta tgatgattcg acctttagat   1800
ttttgaaagc gcaatgtcag aagcgattat gaaagcaaca aagaaatccg agaagctgc    1860
caggtgagaa actgttgaa aacttcagaa gcaaacaata ttgtctccct tccagcaata   1920
agtggtagtt atgtgaagtc accaaggttc ttgaccgtga atctggagcc gtttgagttc   1980
acaagagtct ctacttgggg tgacagtgct cacgtggctc gactatagaa aactccactg   2040
actgtcgggc tttaaaaagg gaagaaactg ctgagcttgc tgtgcttcaa actactactg   2100
gaccttattt tggaactatg gtagccagat gataaatatg gttaatttc                2149
```

<210> SEQ ID NO 2
<211> LENGTH: 498
<212> TYPE: PRT
<213> ORGANISM: Homo sapien

<400> SEQUENCE: 2

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
             20                  25                  30

Tyr Asn Arg Ile Gln His Gly Gln Cys Ala Tyr Thr Phe Ile Leu Pro
         35                  40                  45

Glu His Asp Gly Asn Cys Arg Glu Ser Thr Thr Asp Gln Tyr Asn Thr
     50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
```

```
                100             105             110
Ala Gln Ile Gln Gln Asn Ala Val Gln Asn His Thr Ala Thr Met Leu
            115             120             125
Glu Ile Gly Thr Ser Leu Leu Ser Gln Thr Ala Glu Gln Thr Arg Lys
        130             135             140
Leu Thr Asp Val Glu Thr Gln Val Leu Asn Gln Thr Ser Arg Leu Glu
145             150             155             160
Ile Gln Leu Leu Glu Asn Ser Leu Ser Thr Tyr Lys Leu Glu Lys Gln
                165             170             175
Leu Leu Gln Gln Thr Asn Glu Ile Leu Lys Ile His Glu Lys Asn Ser
            180             185             190
Leu Leu Glu His Lys Ile Leu Glu Met Glu Gly Lys His Lys Glu Glu
        195             200             205
Leu Asp Thr Leu Lys Glu Glu Lys Glu Asn Leu Gln Gly Leu Val Thr
210             215             220
Arg Gln Thr Tyr Ile Ile Gln Glu Leu Glu Lys Gln Leu Asn Arg Ala
225             230             235             240
Thr Thr Asn Asn Ser Val Leu Gln Lys Gln Gln Leu Glu Leu Met Asp
                245             250             255
Thr Val His Asn Leu Val Asn Leu Cys Thr Lys Glu Gly Val Leu Leu
            260             265             270
Lys Gly Gly Lys Arg Glu Glu Lys Pro Phe Arg Asp Cys Ala Asp
        275             280             285
Val Tyr Gln Ala Gly Phe Asn Lys Ser Gly Ile Tyr Thr Ile Tyr Ile
290             295             300
Asn Asn Met Pro Glu Pro Lys Lys Val Phe Cys Asn Met Asp Val Asn
305             310             315             320
Gly Gly Gly Trp Thr Val Ile Gln His Arg Glu Asp Gly Ser Leu Asp
                325             330             335
Phe Gln Arg Gly Trp Lys Glu Tyr Lys Met Gly Phe Gly Asn Pro Ser
            340             345             350
Gly Glu Tyr Trp Leu Gly Asn Glu Phe Ile Phe Ala Ile Thr Ser Gln
        355             360             365
Arg Gln Tyr Met Leu Arg Ile Glu Leu Met Asp Trp Glu Gly Asn Arg
370             375             380
Ala Tyr Ser Gln Tyr Asp Arg Phe His Ile Gly Asn Glu Lys Gln Asn
385             390             395             400
Tyr Arg Leu Tyr Leu Lys Gly His Thr Gly Thr Ala Gly Lys Gln Ser
                405             410             415
Ser Leu Ile Leu His Gly Ala Asp Phe Ser Thr Lys Asp Ala Asp Asn
            420             425             430
Asp Asn Cys Met Cys Lys Cys Ala Leu Met Leu Thr Gly Gly Trp Trp
        435             440             445
Phe Asp Ala Cys Gly Pro Ser Asn Leu Asn Gly Met Phe Tyr Thr Ala
450             455             460
Gly Gln Asn His Gly Lys Leu Asn Gly Ile Lys Trp His Tyr Phe Lys
465             470             475             480
Gly Pro Ser Tyr Ser Leu Arg Ser Thr Thr Met Met Ile Arg Pro Leu
                485             490             495
Asp Phe

<210> SEQ ID NO 3
<211> LENGTH: 2146
```

<210> TYPE: DNA
<213> ORGANISM: Homo sapien

<400> SEQUENCE: 3

```
cagctgactc aggcaggctc catgctgaac ggtcacacag agaggaaaca ataaatctca    60
gctactatgc aataaatatc tcaagtttta acgaagaaaa acatcattgc agtgaaataa   120
aaaattttaa aattttagaa caaagctaac aaatggctag ttttctatga ttcttcttca   180
aacgctttct ttgaggggga aagagtcaaa caaacaagca gttttacctg aaataaagaa   240
ctagttttag aggtcagaag aaaggagcaa gttttgcgag aggcacggaa ggagtgtgct   300
ggcagtacaa tgacagtttt cctttccttt gctttcctcg ctgccattct gactcacata   360
gggtgcagca atcagcgccg aagtccagaa acagtggga gaagatataa ccggattcaa   420
catgggcaat gtgcctacac tttcattctt ccagaacacg atggcaactg tcgtgagagt   480
acgacagacc agtacaacac aaacgctctg cagagagatg ctccacacgt ggaaccggat   540
ttctcttccc agaaacttca acatctggaa catgtgatgg aaaattatac tcagtggctg   600
caaaaacttg agaattacat tgtggaaaac atgaagtcgg agatggccca gatacagcag   660
aatgcagttc agaaccacac ggctaccatg ctggagatag aaccagcct cctctctcag   720
actgcagagc agaccagaaa gctgacagat gttgagaccc aggtactaaa tcaaacttct   780
cgacttgaga tacagctgct ggagaattca ttatccacct acaagctaga gaagcaactt   840
cttcaacaga caaatgaaat cttgaagatc catgaaaaaa acagtttatt agaacataaa   900
atcttagaaa tggaaggaaa acacaaggaa gagttggaca ccttaaagga agagaaagag   960
aaccttcaag gcttggttac tcgtcaaaca tatataatcc aggagctgga aaagcaatta  1020
aacagagcta ccaccaacaa cagtgtcctt cagaagcagc aactggagct gatggacaca  1080
gtccacaacc ttgtcaatct ttgcactaaa gaagttttac taaagggagg aaaaagagag  1140
gaagagaaac catttagaga ctgtgcagat gtatatcaag ctggttttaa taaagtggaa  1200
atctacacta tttatattaa taatatgcca gaacccaaaa aggtgttttg caatatggat  1260
gtcaatgggg gaggttggac tgtaatacaa catcgtgaag atggaagtct agatttccaa  1320
agaggctgga aggaatataa aatgggtttt ggaaatccct ccggtgaata ttggctgggg  1380
aatgagttta ttttttgccat taccagtcag aggcagtaca tgctaagaat tgagttaatg  1440
gactgggaag ggaaccgagc ctattcacag tatgacagat tccacatagg aaatgaaaag  1500
caaaactata ggttgtattt aaaaggtcac actgggacag caggaaaaca gagcagcctg  1560
atcttacacg gtgctgattt cagcactaaa gatgctgata atgacaactg tatgtgcaaa  1620
tgtgccctca tgttaacagg aggatggtgg tttgatgctt gtggcccctc caatctaaat  1680
ggaatgttct atactgcggg acaaaaccat cgaaaactga atgggataaa gtggcactac  1740
ttcaaagggc ccagttactc cttacgttcc acaactatga tgattcgacc tttagatttt  1800
tgaaagcgca atgtcagaag cgattatgaa agcaacaaag aaatccggag aagctgccag  1860
gtgagaaact gtttgaaaac ttcagaagca aacaatattg tctcccttcc accaataagt  1920
ggtagttatg tgaagtcacc aaggttcttg accgtgaatc tggagccgtt tgagttcaca  1980
agagtctcta cttggggtga cagtgctcac gtggctcgac tatagaaaac tccactgact  2040
gtcgggcttt aaaaagggaa gaaactgctg agcttgctgt gcttcaaact actactggac  2100
cttattttgg aactatggta gccagatgat aaatatggtt aatttc              2146
```

<210> SEQ ID NO 4

<211> LENGTH: 497
<212> TYPE: PRT
<213> ORGANISM: Homo sapien

<400> SEQUENCE: 4

```
Met Thr Val Phe Leu Ser Phe Ala Phe Leu Ala Ala Ile Leu Thr His
  1               5                  10                  15

Ile Gly Cys Ser Asn Gln Arg Arg Ser Pro Glu Asn Ser Gly Arg Arg
             20                  25                  30

Tyr Asn Arg Ile Gln His Gly Gln Cys Ala Tyr Thr Phe Ile Leu Pro
         35                  40                  45

Glu His Asp Gly Asn Cys Arg Glu Ser Thr Thr Asp Gln Tyr Asn Thr
     50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
        130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Val Leu Leu Lys
            260                 265                 270

Gly Gly Lys Arg Glu Glu Lys Pro Phe Arg Asp Cys Ala Asp Val
        275                 280                 285

Tyr Gln Ala Gly Phe Asn Lys Ser Gly Ile Tyr Thr Ile Tyr Ile Asn
    290                 295                 300

Asn Met Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Arg Gly Trp Lys Glu Tyr Lys Met Gly Phe Gly Asn Pro Ser Gly
            340                 345                 350

Glu Tyr Trp Leu Gly Asn Glu Phe Ile Phe Ala Ile Thr Ser Gln Arg
        355                 360                 365

Gln Tyr Met Leu Arg Ile Glu Leu Met Asp Trp Glu Gly Asn Arg Ala
    370                 375                 380

Tyr Ser Gln Tyr Asp Arg Phe His Ile Gly Asn Glu Lys Gln Asn Tyr
```

```
                385                 390                 395                 400
Arg Leu Tyr Leu Lys Gly His Thr Gly Thr Ala Gly Lys Gln Ser Ser
                405                 410                 415
Leu Ile Leu His Gly Ala Asp Phe Ser Thr Lys Asp Ala Asp Asn Asp
                420                 425                 430
Asn Cys Met Cys Lys Cys Ala Leu Met Leu Thr Gly Trp Trp Phe
                435                 440                 445
Asp Ala Cys Gly Pro Ser Asn Leu Asn Gly Met Phe Tyr Thr Ala Gly
                450                 455                 460
Gln Asn His Arg Lys Leu Asn Gly Ile Lys Trp His Tyr Phe Lys Gly
465                 470                 475                 480
Pro Ser Tyr Ser Leu Arg Ser Thr Thr Met Met Ile Arg Pro Leu Asp
                485                 490                 495
Phe

<210> SEQ ID NO 5
<211> LENGTH: 2282
<212> TYPE: DNA
<213> ORGANISM: Homo sapien

<400> SEQUENCE: 5
gaattcctgg gttggtgttt atctcctccc agccttgagg gagggaacaa cactgtagga      60
tctggggaga gaggaacaaa ggaccgtgaa agctgctctg taaaagctga cacagccctc     120
ccaagtgagc aggactgttc ttcccactgc aatctgacag tttactgcat gcctggagag     180
aacacagcag taaaaaccag gtttgctact ggaaaaagag gaaagagaag actttcattg     240
acggacccag ccatggcagc gtagcagccc tgcgtttcag acggcagcag ctcgggactc     300
tggacgtgtg tttgccctca gtttgctaa gctgctggtt tattactgaa gaaagaatgt      360
ggcagattgt tttctttact ctgagctgtg atcttgtctt ggccgcagcc tataacaact     420
tcggaagag catggacagc ataggaaaga agcaatatca ggtccagcat gggtcctgca      480
gctacacttt cctcctgcca gagatggaca actgccgctc ttcctccagc ccctacgtgt     540
ccaatgctgt gcagagggac gcgccgctcg aatacgatga ctcggtgcag aggctgcaag     600
tgctggagaa catcatggaa acaacactc agtggctaat gaagcttgag aattatatcc      660
aggacaacat gaagaaagaa atggtagaga tacagcagaa tgcagtacag aaccagacgg     720
ctgtgatgat agaaataggg acaaacctgt tgaaccaaac agctgagcaa acgcggaagt     780
taactgatgt ggaagcccaa gtattaaatc agaccacgag acttgaactt cagctcttgg     840
aacactccct ctcgacaaac aaattggaaa acagattttt ggaccagacc agtgaaataa     900
acaaattgca agataagaac agtttcctag aaaagaaggt gctagctatg gaagacaagc     960
acatcatcca actacagtca ataaaagaag agaagatca gctacaggtg ttagtatcca    1020
agcaaaattc catcattgaa gaactagaaa aaaaatagt gactgccacg gtgaataatt     1080
cagttcttca aaagcagcaa catgatctca tggagacagt taataactta ctgactatga     1140
tgtccacatc aaactcagct aaggacccca ctgttgctaa agaagaacaa atcagcttca     1200
gagactgtgc tgaagtattc aaatcaggac acaccacaaa tggcatctac acgttaacat     1260
tccctaattc tacagaagag atcaaggcct actgtgacat ggaagctgga ggaggcgggt     1320
ggacaattat tcagcgacgt gaggatggca gcgttgattt tcagaggact ggaaagaat      1380
ataaagtggg atttggtaac ccttcaggag aatattggct gggaaatgag tttgtttcgc     1440
aactgactaa tcagcaacgc tatgtgctta aaatacacct taaagactgg gaagggaatg     1500
```

```
aggcttactc attgtatgaa catttctatc tctcaagtga agaactcaat tataggattc    1560
accttaaagg acttacaggg acagccggca aaataagcag catcagccaa ccaggaaatg    1620
attttagcac aaaggatgga gacaacgaca aatgtatttg caaatgttca caaatgctaa    1680
caggaggctg gtggtttgat gcatgtggtc cttccaactt gaacggaatg tactatccac    1740
agaggcagaa cacaaataag ttcaacggca ttaaatggta ctactggaaa ggctcaggct    1800
attcgctcaa ggccacaacc atgatgatcc gaccagcaga tttctaaaca tcccagtcca    1860
cctgaggaac tgtctcgaac tattttcaaa gacttaagcc cagtgcactg aaagtcacgg    1920
ctgcgcactg tgtcctcttc caccacagag ggcgtgtgct cggtgctgac gggacccaca    1980
tgctccagat tagagcctgt aaactttatc acttaaactt gcatcactta acggaccaaa    2040
gcaagaccct aaacatccat aattgtgatt agacagaaca cctatgcaaa gatgaacccg    2100
aggctgagaa tcagactgac agtttacaga cgctgctgtc acaaccaaga atgttatgtg    2160
caagtttatc agtaaataac tggaaaacag aacacttatg ttatacaata cagatcatct    2220
tggaactgca ttcttctgag cactgtttat acactgtgta aatacccata tgtcctgaat    2280
tc                                                                   2282
```

<210> SEQ ID NO 6
<211> LENGTH: 496
<212> TYPE: PRT
<213> ORGANISM: Homo sapien

<400> SEQUENCE: 6

```
Met Trp Gln Ile Val Phe Phe Thr Leu Ser Cys Asp Leu Val Leu Ala
  1               5                  10                  15

Ala Ala Tyr Asn Asn Phe Arg Lys Ser Met Asp Ser Ile Gly Lys Lys
                 20                  25                  30

Gln Tyr Gln Val Gln His Gly Ser Cys Ser Tyr Thr Phe Leu Leu Pro
             35                  40                  45

Glu Met Asp Asn Cys Arg Ser Ser Ser Pro Tyr Val Ser Asn Ala
         50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
        130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220
```

-continued

```
Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
            245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
            450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```